United States Patent [19]

Ecke

[11] 4,117,168
[45] Sep. 26, 1978

[54] ANTIFUNGAL DI(ARYL)METHYL ALKYL SULFONES

[75] Inventor: George G. Ecke, Barberton, Ohio

[73] Assignee: PPG Industries, Inc., Pittsburgh, Pa.

[21] Appl. No.: 867,418

[22] Filed: Jan. 6, 1978

Related U.S. Application Data

[60] Division of Ser. No. 703,168, Jul. 7, 1976, Pat. No. 4,067,909, which is a continuation-in-part of Ser. No. 578,598, May 19, 1978, abandoned.

[51] Int. Cl.² ............................................. A01N 9/14
[52] U.S. Cl. .................................................. 424/337
[58] Field of Search ................. 260/607 AR; 424/337

[56] References Cited

U.S. PATENT DOCUMENTS

| | | | |
|---|---|---|---|
| 2,618,640 | 11/1952 | Archer et al. | 260/293.4 |
| 3,016,403 | 1/1962 | Dodson | 260/607 |
| 3,054,719 | 9/1972 | Hendrik et al. | 424/337 |
| 3,412,149 | 11/1968 | Schlor et al. | 260/556 |
| 3,415,887 | 12/1968 | Keogh et al. | 260/607 |
| 3,465,044 | 9/1969 | Hirano et al. | 260/607 |
| 3,466,377 | 9/1969 | Shunk et al. | 424/337 |
| 3,549,702 | 12/1970 | Loev | 260/556 |
| 3,615,745 | 10/1971 | Crovetti et al. | 260/607 X |
| 3,624,094 | 11/1971 | Gautier et al. | 260/607 A X |
| 3,637,803 | 1/1972 | Shen et al. | 260/607 A |
| 3,689,567 | 9/1972 | Shen et al. | 260/607 A |

FOREIGN PATENT DOCUMENTS

1,178,279  1/1970  United Kingdom.

OTHER PUBLICATIONS

Chem. Abstracts, vol. 72 (1970), p. 3223x
Chem. Abstracts, vol. 56 (1962), p. 15335b
Klenk, et al., JACS, vol. 70 (1948), p. 3846–3850.
Metcalf et al., "Bull. World Health Org.," vol. 38 (1968), p. 633–647.

*Primary Examiner*—V. D. Turner
*Attorney, Agent, or Firm*—Robert J. Grassi

[57] ABSTRACT

Sulfones of Bis(4-chlorophenyl) or 2,4′-dichlorodiphenylmethyl and alkyls with one to four carbon atoms, e.g., bis(4-chlorophenyl)methyl methyl sulfone, which control the harmful effects of Piricularia fungus, particularly *Piricularia oryzae*, upon plants are disclosed. Also disclosed are the methods of controlling the harmful effects of these fungi with these sulfones, as well as other fungi, such as Uromyces and Venturia genera with bis(4-chlorophenyl)methyl methyl sulfone.

20 Claims, No Drawings

ANTIFUNGAL DI(ARYL)METHYL ALKYL SULFONES

CROSS REFERENCE TO RELATED APPLICATIONS

This is a division of the allowed copending application Ser. No. 703,168, filed July 7, 1976, now U.S. Pat. No. 4,067,909 which is a continuation-in-part of abandoned application Ser. No. 578,598, filed May 19, 1975.

BACKGROUND OF THE INVENTION

1. Field of the Invention

The invention relates to compounds of di(aryl)methyl alkyl sulfones composed of bis(4-chlorophenyl), or 2,4'-dichlorodiphenylmethyl and alkyls with one to four carbon atoms, and to methods of controlling the harmful effects of fungi upon plants with these compounds, particularly Piricularia fungi.

2. Description of the Prior Art

Because fungus causes harmful effects such as disease which affect every crop and ornamental plant, chemical compounds are required which prevent or eradicate these diseases. The action of a chemical towards a specific disease is not a priori predictable because of very complicated biochemical reactions. For example a compound may act as a respiratory enzyme which causes respiratory malfunction in the attacking plant pest, or as a hormone to stimulate a rapid growth which causes the plant pest to rapidly die, or as a metabolite within the plant which stimulates the plant to fight off the disease or kill the pest.

Fungus of the genus Piricularia, particularly the fungus *Piricularia oryzae*, which affects rice causing Rice Blast Disease, is a fungus which needs to be controlled. Although certain sulfides, sulfoxides and sulfones possess biochemical activity against certain organisms, as shown in the following prior art; nothing therein suggests controlling the harmful effects of Piricularia fungus with sulfones.

Bis(4-chlorophenyl)methyl methyl sulfide is active against the mosquito species, *Anopheles albimanus*, as described by R. L. Metcalf et al, *Bulletin of the World Health Organization*, Vol. 38, pages 633–647, (1968). Phenylmercaptomethane sulfonamide is described as being active against *Phytophthora infestans* (U.S. Pat. No. 3,412,149). Oximidomethane sulfonamides are disclosed as being active against bacteria and weeds (U.S. Pat. 3,549,702). 4-Methoxyphenyl diiodomethyl sulfone is shown to inhibit the growth of *Aspergillus oryzae* (U.S. Pat. No. 3,615,745), and 2,4,5,4'-tetrachlorodiphenyl sulfide, sulfoxide, and sulfones are shown to be effective against Red Spider Mites (U.S. Pat. No. 3,054,719). Other sulfones, sulfides, and sulfoxides are described but their activity against fungus are not known. For example, compounds of type B-X-C(Ar) (Ar')-SO₂-R wherein B is a lower aliphatic tertiary-amino group, X is a lower alkylene group, Ar and Ar' are aryl groups and R is an alkyl group, are claimed as analgetics. 4,4'-dichlorodiphenyl sulfone is claimed as an important monomer for preparing polyarylene polyethers (Belgian Pat. No. 650,476). Certain aryl sulfoxides are described by C. Shunk et al. (U.S. Pat. No. 3,466,377) as being analgetics. Other aryl sulfones are described as both analgetics and anti-pyretics by C. Shunk et al. (U.S. Pat. No. 3,637,803 and U.S. Pat. No. 3,689,567), Jean A. Gautier et al. in U.S. Pat. No. 3,624,094 describes alpha-[(phenyl sulfinyl)methyl]-alpha phenyl derivatives of pyridinemethanols as analgetics and anti-inflammatory agents.

SUMMARY OF THE INVENTION

Novel compositions represented by the general formula

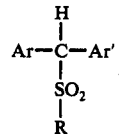

in which Ar is 4-chlorophenyl, Ar' is 2- or 4-chlorophenyl and R is an alkyl of from one to four carbon atoms are active against the harmful effects of fungi of the genus Piricularia upon plants, particularly the specie *Piricularia oryzae*. Bis(4-chlorophenyl)methyl methyl sulfone is particularly effective against Piricularia, especially *Piricularia oryzae*. It is also effective against fungi of the genus Uromyces, Melampsora, Puccinia, Cochliobolus, Erysiphe, and Venturia.

DESCRIPTION OF THE PREFERRED EMBODIMENTS

The novel compounds of bis(aryl)methyl alkyl sulfones are represented by the general formula:

in which Ar is 4-chlorophenyl(p-chlorophenyl), Ar' is an aryl of 2- or 4-chlorophenyl(o- or p-chlorophenyl), and R is an alkyl of from one to four carbon atoms. When Ar' is 2-chlorophenyl, the compound of the general formula (VI) is called 2,4'-dichlorodiphenylmethyl methyl sulfone, and is so-called herein and in the claims. The phrase "an alkyl of from one to four carbon atoms" as used herein and in the claims refers to: methyl, ethyl, n-propyl, isopropyl, n-butyl, sec-butyl, and tert-butyl. Examples of these compounds are: bis(4-chlorophenyl)-methyl tert-butyl sulfone, 2,4'-dichlorodiphenylmethyl methyl sulfone, and 2,4'-dichlorodiphenylmethyl sec-butyl sulfone. Preferably, the alkyl is methyl, ethyl, n-propyl, isopropyl, and n-butyl. Examples of compounds with these preferred alkyls are:

Bis(4-chlorophenyl)methyl methyl sulfone;
Bis(4-chlorophenyl)methyl ethyl sulfone;
Bis(4-chlorophenyl)methyl n-propyl sulfone;
Bis(4-chlorophenyl)methyl isopropyl sulfone;
Bis(4-chlorophenyl)methyl n-butyl sulfone;
2,4'-dichlorodiphenylmethyl methyl sulfone;
2,4'-dichlorodiphenylmethyl ethyl sulfone;
2,4'-dichlorodiphenylmethyl n-propyl sulfone;
2,4-dichlorodiphenylmethyl isopropyl sulfone; and
2,4'-dichlorodiphenylmethyl n-butyl sulfone.

Those compounds in which Ar and Ar' are 4-chlorophenyl and R is one of the preferred alkyls, mentioned herein, are highly preferred.

The compounds of bis(4-chlorophenyl)methyl methyl sulfone, 2,4'-dichlorodiphenylmethyl methyl sulfone, bis(4-chlorophenyl)methyl n-butyl-sulfone, and 2,4'-dichlorodiphenylmethyl n-butyl sulfone are especially preferred.

a. Synthesis of the Compounds

The sulfone compounds are synthesized by oxidation of the corresponding sulfide compounds. The sulfide compounds are made by well known organic synthesis routes of hydrogenation of ketones, substitution of the hydroxyl group by a halogen or other group easily substituted by mercaptan. Oxidation of the sulfur atom of the sulfide compound with hydrogen peroxide or a peroxy acid gives the sulfone compound. All of these synthesis steps are shown by the general reaction scheme, in which Ar, Ar' and R have the same meaning described hereinbefore, X represents a halogen or other group which can be easily substituted by the mercaptan HSR, and (O) represents the oxidizing agent, e.g., hydrogen peroxide.

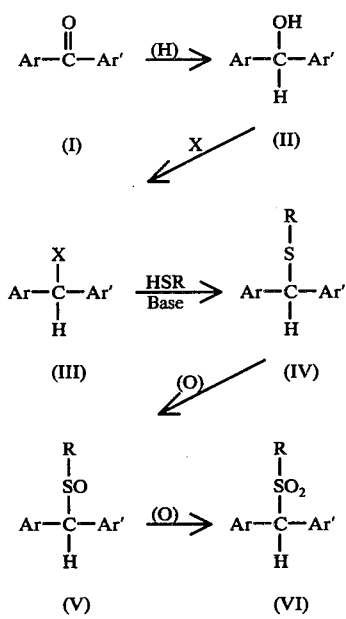

The following examples represent the synthesis of the compounds described herein by the above mentioned reaction scheme.

EXAMPLE I

SYNTHESIS OF BIS(P-CHLOROPHENYL)METHYL METHYL SULFIDE, SULFOXIDE, AND SULFONE

Hydrogenation of 4,4'-Dichlorobenzophenone (I) to 4,4'-Dichlorobenzhydrol (II)

Sodium borohydride (0.164 mole) 6.25 grams in 300 ml. of ethanol was slowly added (over a 30 minute period) to a refluxing solution of 74.3 grams (0.296 mole) of 4,4'-dichlorobenzophenone (Eastman 1440) in 250 ml. of ethanol, and refluxing was continued for an additional 30 minutes. Then a 100 ml. aqueous solution containing 43.5 grams of acetic acid was added dropwise until hydrogen evolution stopped, whereupon the remainder was rapidly added. A white precipitate formed and was collected by filtration. A 300 ml. aqueous slurry containing this precipitate was warmed to above 95° C., cooled, and filtered, and 74.1 grams (99 percent) of a white solid product (4,4'-dichlorobenzhydrol) having a melting point of 92.5°–94° C. was obtained.

Preparation of Chloro-bis(p-chlorophenyl)methane (III)

A solution of 60.02 grams (0.237 mole) of the 4,4'-dichlorobenzhydrol (prepared above) in 175 ml. of toluene, was refluxed and traces of water removed as the toluene-water azeotrope; then 42 grams (0.356 mole) of thionyl chloride under anhydrous conditions was slowly added during a 1 hour period. The solution was refluxed and excess thionyl chloride removed by distillation. The remaining solvent was removed by distillation under vacuum.

The crude product (68.9 grams) was recrystallized twice from 2,2,4-trimethylpentane to give 49.2 grams (76 percent) of chloro-bis(p-chlorophenyl)methane, melting point 61.5°–62.5° C.

Preparation of Bis(p-chlorophenyl)methyl methyl sulfide (IV)

Chloro-bis(p-chlorophenyl)methane (0.130 mole, 35.2 grams) was added to a cold sodium mercaptide solution formed by distilling 0.205 mole (9.8 grams) of methyl mercaptan into a stirred, cooled solution (0° C.) of ethanolic sodium ethoxide (157 ml., 1.038 N, 0.163 grams). Upon warming, a precipitate of sodium chloride formed, and after refluxing this mixture for 2 hours and then mixing with water, an oil formed which was extracted with three portions of methylene chloride (30 ml.). The methylene chloride solvent was distilled off under vacuum, leaving 36.7 grams (100 percent) of a white solid with a melting point of 55.5–57° C. Recrystallization from 2,2,4-trimethylpentane at 0° C. gave a 92 percent yield of the white solid bis(p-chlorophenyl)methyl methyl sulfide (melting point 56°–57° C.).

Analysis Calculated For: $C_{14}H_{12}Cl_2S$: C, 59.37; H, 4.27; and S, 11.32 Found: C, 59.25; H, 4.20; and S, 11.1

Preparation of Bis(p-chlorophenyl)methyl methyl sulfoxide (V)

A solution of 10.7 grams (0.0525 mole) of m-chloroperbenzoic acid in 150 ml. of chloroform was slowly added to a cool solution (5°–7° C.) of 14.1 grams (0.050 mole) of bis(p-chlorophenyl)methyl methyl sulfide in 500 ml. of chloroform, and the resulting solution stirred for 2 hours at a temperature of 5° C., while a white precipitate formed. The mixture after warming to ambient temperature and holding at this temperature for a two hour period was then mixed with a solution having 20 grams of potassium carbonate in 200 ml. of water. The chloroform phase was then removed and washed with 100 ml. of water, and the chloroform distilled off; the vacuum distillation leaving 14.7 grams of a crude product which was recrystallized twice from 2,2,4-trimethylpentane-benzene (2:1) mixture to yield 11.7 grams (78 percent) of the white colored solid of bis(p-chlorophenyl)methyl methyl sulfoxide with a melting point of 109.5°–110.5° C.

Analysis Calculated For: $C_{12}H_{12}Cl_2OS$: C, 56.19; H, 4.04; and S, 10.72 Found: C, 56.18; H, 4.04; and S, 10.5

Preparation of Bis(p-chlorophenyl)methyl methyl sulfone (VI)

A 250 ml. chloroform solution containing 20.1 grams (0.105 mole) of m-chloroperbenzoic acid was slowly added over a 25 minute period to 250 ml. of a cool (5° C). chloroform solution containing 14.1 grams (0.050 mole) of bis(p-chlorophenyl)methyl methyl sulfide. The temperature of 5° C. was maintained for two hours and then the solution was mixed with an aqueous solution of 40 grams of potassium carbonate in 200 ml. of water, the chloroform phase was removed, washed with water, and the chloroform distilled off. The product was recrystallized from a 2,2,4-trimethylpentane-benzene mixture (three times) and then dissolved in methanol. The methanol was distilled off and the crystals which remained were recrystallized a second time from methanol to give 8.7 grams (56 percent yield) of white crystals of bis(p-chlorophenyl)methyl methyl sulfone, melting point 93°-94.5° C.

Analysis Calculated For: $C_{14}H_{12}Cl_2O_2S$: C, 53.34; H, 3.83; and S, 10.17 Found: C, 53.32; H, 3.83; and S, 10.1

Preparation of Bis(p-methoxyphenyl)methyl methyl sulfide (IV)

4,4'-Dimethoxybenzhydryl chloride (0.0538 mole, 14.53 grams) was slowly added to a stirred, cooled (5°-10° C.) 70 ml. (1.018 N) sodium ethylate solution containing 0.15 mole (7.2 grams) of methyl mercaptan. After a white precipitate formed, the mixture was warmed to room temperature and refluxed for one hour, then reacted with 700 ml. of water and extracted with methylene chloride. The methylene chloride extract was washed with water, and the methylene chloride removed by vacuum distillation leaving 14.6 grams of white crystals which were recrystallized from hexane-ether mixture to give 12.6 grams (85 percent yield) of bis(p-methoxyphenyl)methyl methyl sulfide (melting point 62°-63° C.).

Analysis Calculated For: $C_{16}H_{18}O_2S$: C, 70.04; H, 6.61; and S, 11.9 Found: C, 70.06; H, 6.43; and S, 11.4

Preparation of Bis(p-methoxyphenyl)methyl methyl sulfoxide (V)

A 50 ml. chloroform solution of 0.014 mole (2.4 grams) of m-chloroperbenzoic acid was slowly added to a stirred, cooled (0° C.), 25 ml. chloroform solution of 3.4 grams (0.0125 mole) of bis(p-methoxyphenyl)methyl methyl sulfide. The solution was kept at 0° C. for 2.5 hours, then warmed to an ambient temperature and maintained there for 2.5 hours, washed with 100 ml. of 10 percent aqueous potassium carbonate solution, 100 ml. of water and dried with $Na_2SO_4$. The solvent was removed to give 3.8 grams (105 percent yield) of a pale yellow viscous liquid which crystallized upon standing to an impure, low melting solid (about 90 percent purity) of bis(p-methoxyphenyl)methyl methyl sulfoxide.

EXAMPLE II

SYNTHESIS OF BIS(P-CHLOROPHENYL)METHYL N-BUTYL SULFIDE, SULFOXIDE, AND SULFONE

Preparation of Bis(p-chlorophenyl)methyl n-butyl sulfide

The procedure described for making bis(p-chlorophenyl)methyl methyl sulfide was followed except that n-butyl mercaptan was used. The product obtained was greater than 90 percent pure.

Analysis Calculated For: $C_{17}H_{18}Cl_2S$: C, 62.77; H, 5.58 Found: C, 62.67 and H, 5.57

Preparation of Bis(p-chlorophenyl)methyl n-butyl sulfoxide

The procedure for making bis(p-chlorophenyl)methyl methyl sulfone was followed, using a slight excess of m-chloroperbenzoic acid (0.027 mole acid to 0.025 mole of bis(p-chlorophenyl)methyl n-butyl sulfoxide). A light amber liquid was formed and this gave crystals which were recrystallized from methanol as a white solid of bis(p-chlorophenyl)methyl n-butyl sulfoxide, melting point 116°-188° C.

Analysis Calculated For: $C_{17}H_{18}Cl_2S$: C, 59.82 and H, 5.32 Found: C, 59.78 ± 0.5 and H, 5.31 ± .05

Preparation of Bis(p-chlorophenyl)methyl n-butyl sulfone

The procedure for making bis(p-chlorophenyl)methyl butyl sulfoxide was followed except that the amount of m-chloroperbenzoic acid was doubled. A pale amber liquid formed which crystallized upon standing. Recrystallization from methanol (80 percent yield) gave a white solid of bis(p-chlorophenyl)methyl n-butyl sulfone with a melting point of 104°-106° C.

Analysis Calculated For: $C_{17}H_{18}Cl_2S$: C, 57.15 and H, 5.08 Found: C, 57.73 ± 0.8 and H, 5.45 ± .08

In the synthesis any suitable solvent may be used in which the reaction materials may dissolve, such as benzene, etc. but preferably those solvents are used in which the reaction products will precipitate from, or which are readily distilled from the product. The purification of the product is desirable but not necessary, for these compounds when used as fungicides, or in other agriculturally suitable compositions may contain impurities, in fact they may have from 1 to 90 weight percent of impurities.

The ketones of the general formula

wherein Ar and Ar' are the aryls mentioned herein are preferably synthesized by the reaction of chlorobenzene and phosgene, followed by separation of the bis(p-chlorophenyl) ketone and 2,4'-dichlorodiphenyl ketone. However, the mixture of bis(p-chlorophenyl) ketone and 2,4'-dichlorodiphenyl ketone can be used together for synthesis according to the general reaction described herein, of sulfone mixtures containing bis(p-chlorophenyl)methyl alkyl sulfone and 2,4'-dichlorodiphenylmethyl alkyl sulfone, which are then separated, or used together.

b. Properties of the Compounds

The following examples illustrate the biological activity of the sulfone compounds, particularly against the harmful effect of the fungus *Piricularia oryzae*, which causes Rice Blast Disease, a prevalent disease occurring throughout the world.

PROCEDURE

This test shows the protectant properties of the compound, that is the property to prevent plants from the harmful effects (disease) caused by the fungus *Piricularia oryzae*.

In this test, rice plants (Nato variety), were grown under natural sunlight in a glass covered greenhouse at 70° to 80° F. amd 50 to 90 percent relative humidity for 18 days until a fully developed second stage leaf was attained. The test plants were mounted on a compound turntable and sprayed to incipient run off at 40 pounds pressure for 60 seconds, equivalent to 50 gallons per acre, using a solid cone, T-Jet 8001-E spray nozzle with a solution containing 1000 parts per million (ppm) of the test compound.

The spray solution was formed by dissolving a predetermined amount of test compound in a stock solution, the volume of which is equivalent to 19 percent by volume of the total spray volume, and diluting the volume of stock solution to the required volume with distilled water. The stock solution for dissolving the compound for testing is an acetone emulsion solution, containing 1995 ml. acetone, 4 ml. SPAN 85 ® (sorbitan trioleate), and 1 ml. TWEEN 80 ® (sorbitan monooleate polyalkylene derivative).

After the treated plants had dried, (4–8 hours), they were inoculated by uniformly spraying at a rate of 200 milliliters per 70 plants with a suspension containing 105 spores per milliliter of the fungus *Piricularia oryzae,* taken directly from diseased plants. Then the plants were incubated in the dark for 40 hours at 80° F. and 95 percent or more relative humidity, which normally insures that the spores have a chance to infest the plants. The plants were then placed in a glass greenhouse, using natural sunlight, and observed for signs of dark black to grey spots visible to the naked eye (normal infestation stage and generally occurring after 5 days). The greenhouse operates at a temperature from 70° to 80° F. and a humidity range of from 50 to 90 percent.

The severity of the disease was determined by actual count of the developed spots on inoculated but otherwise untreated controls. The test results are expressed as Control Effectiveness, which is determined by actual count of the number of developed spots appearing on the respectively treated plants compared directly to equivalent developed spots on inoculated but otherwise untreated controls. This control effectiveness is expressed as Percent Control which is calculated as follows:

$$\text{Percent Control} = \left[1.00 - \frac{\text{Ave. No. Spots On All Treated Plants}}{\text{Ave. No. Spots On All Untreated Plants}}\right] \times 100$$

The Percent Control value is based on at least three replicate tests (70 plants per replicate).

The Percent Control obtained at 1000 ppm for the compounds are shown in Table I. Column 1, gives the example number; column 2, gives the compound which was synthesized as described herein unless indicated otherwise; and column 3, gives the percent control at 1000 parts per million (ppm) of the compound. Values over twenty percent indicate protectant control.

TABLE I

PERCENT CONTROL OF RICE BLAST DISEASE AT 1000 PPM APPLIED AS A PROTECTANT

| Example No. | Compound Name | Percent Control |
|---|---|---|
| III | bis(4-chlorophenyl)methyl methyl sulfone | 99:3B |
| IV | bis(4-chlorophenyl)methyl butyl sulfone | 63:0 |
| V | bis(phenyl)methyl methyl sulfone[a] | 10:0 |

[a]known compound described in U.S. 2,618,640 c. APPLICATION

1. Method of Controlling the Harmful Effects of a Fungus

The harmful effects of a fungus upon a plant are controlled by contacting the plant with a compound of the general formula described herein in an amount effective to control the harmful effects of the fungus upon the plant.

The phrase "contacting the plant with a compound" as used herein and in the claims refers to any method of causing one or more of the compounds described herein to contact the plant. Preferably the plant is contacted with the compound prior to infestation by one or more fungi (e.g., by protectant application). However, the plant can be infested with a fungus described herein prior to contacting the plant or both the plant and fungus with one or more of the compounds described herein (eradicant application).

This contact can be brought about by any known methods of applying compositions to plants, e.g., by spraying a solution, an emulsion, dusting with a dust consisting of granules of a compound or with granules of inert materials coated with one or more of the compounds. The compound can be applied once, or several times over the growing period of the plants to insure protection or eradication of the harmful effects of one or more fungi. Generally the foliage of the plant is contacted.

The phrase "in an amount effective to control the harmful effects of the fungus upon the plant" as used herein and in the claims refers to that amount of compound, expressed as active ingredient, of the formulation applied to the plant, necessary to control the harmful effects of the fungus or fungi. This amount will vary in accordance with the number of plants, the temperature, the severity of the disease in the growth area, but in general is from 250 parts per million to maximum tolerated by the plant, that is which does not severely injure the plant; this is around 20,000 parts per million. Normally from 300 parts per million to 10,000 parts per million are used, and under favorable environmental conditions, particularly with the preferred compounds from 300 parts per million to 2000 parts per million are used, and in many applications from 500 parts per million to 1500 parts per million will suffice for effective control.

The phrase "to control the harmful effects of the fungus upon the plant" as used herein and in the claims means that a smaller percentage of plants chemically treated with a compound described herein are affected by the fungus (have the disease caused by the fungus) as compared to plants which are not chemically treated. The percentage of plants not affected by the fungus will be from 25 to 100 percent of the total plants.

2. Control of Fungi of the Genus Piricularia

The compounds of the general formula described herein are useful to control one or more fungi of the genus Piricularia.

Those compounds in which R is one of the preferred alkyls mentioned herein are more suitable for use against fungus of the genus Piricularia, especially against the specie *Piricularia oryzae.* Especially useful are the compounds in which Ar is 4-chlorophenyl and R is one of the preferred alkyls mentioned herein. Bis(4-chlorophenyl)methyl methyl sulfone is especially useful against fungus of the genus Piricularia, especially as a protectant and eradicant of the specie *Piricularia oryzae.*

3. Suitable Agriculture Formulations

When using compounds of the general formula described herein against one or more fungi mentioned herein, a single compound or several compounds of the general formula may be directly applied to the plant or plant and fungus.

When a compound of the general formula such as bis(p-chlorophenyl)methyl methyl sulfone is used alone, it may be formulated as a granule of relatively large size. When used together with one or more other compounds of the general formula, each of the compounds may be formulated as granules of relatively large size, or each granule itself may contain a mixture of the compounds.

However, it is preferably to formulate one or more of the compounds in combination with other ingredients to make a suitable agricultural composition for contacting the plant (protectant application), or plant and fungus (eradicant application), particularly for contacting the foliage of the plant.

Suitable agricultural compositions containing one or more of the compounds of the general formula, may also contain other pesticides, fungicides, or bactericides which are compatible with the compound or compounds, so that by means of one application the plants are protected against several plant pests.

In these formulations a compound of the general formula will comprise from 0.1 to 99 weight percent of the formulation, or the mixture of compounds of the general formula will comprise from 0.1 to 99 weight percent of the formulation.

4. Methods of Controlling the Harmful Effects of Other Fungi With the Bis(p-chlorophenyl)methyl methyl sulfone The harmful effects of a fungus of the genera of Venturia, Uromyces, Puccinia, Melampsora, Phytophthora, and Cochliobolus (Helminthosporium) are also controlled by contacting the plants with bis(4-chlorophenyl)methyl methyl sulfone in an amount effective to control the harmful effects of the fungus upon the plants.

Bis(4-chlorophenyl)methyl methyl sulfone is especially effective to control the harmful effects (diseases) caused by the following fungi species: *Venturia inaequalis* (Apple Scab), *Uromyces phaseoli typica* (Bean Rust), *Puccinia carthami* (Safflower Rust), *Puccinia rubigo-vera* (Leaf Rust of Wheat), *Phytophthora infestans* (Late Blight of Tomatoes), *Melampsora limi* (pera.) Desmoz. (Flat Rust), and *Cochliobolus herterostrophus* (*Helminthosporium maydis*) (Southern Corn Leaf Blight). The control of the harmful effects of the fungi species and genera mentioned above are generally achieved by contacting the plant with bis(p-chlorophenyl)methyl methyl sulfone prior to the plant being infested with the fungus (protectant application).

The harmful effects of a fungus of the genera Puccinia and Venturia may also be controlled by contacting the plant or both plant and fungus after the plant is infested with the fungus (eradicant application), particularly when the fungus specie is *Puccinia rubigo-vera*, or *Venturia inaequalis*.

A suitable agricultural formulation in the form of a solution is composed of one or more solvents in which a compound or mixture of the compounds are completely soluble. Such solution should contain a surfactant such as TWEEN 20 ®, to increase the wettability of the solution. Other solutions would be aerial spray formulations such as pressurized spray solutions, e.g., aerosols, which use one or more low boiling dispersants solvents such as Freon. The amount of the compound or mixture of the compounds in the solution will depend upon its or their solubility which is effected by the temperature and other ingredients. In solutions of mixtures of the compounds with bis(p-chlorophenyl)methyl methyl sulfone, it comprises from 20 to 90 weight percent of the mixture.

Dusts, which also are suitable agricultural compositions, are mixtures of an active compound, e.g., bis(p-chlorophenyl)methyl methyl sulfone, with one or more finely powdered solids, having an average particle size of less than 50 microns, such as talc, attapulgite, clay, kieselguhr, and other organic and inorganic solids which act as dispersants and carriers for the compound. The weight of bis(p-chlorophenyl)methyl methyl sulfone in a typical dust formulation will be from 1.00 to 10.0 weight percent of the formulation and the balance of the composition is divided between the other ingredients.

When bis(p-chlorophenyl)methyl methyl sulfone is formulated together with one or more compounds of the general formula as a dust composition, these dust compositions also contain other useful agricultural ingredients. In such compositions, bis(p-chlorophenyl)methyl methyl sulfone is generally between 0.5 to 20 parts by weight of the composition, and preferably is from 10 to 90 weight percent of the compound mixture used in these formulations.

In applicable situations these dust formulations may be formulated for aerial spraying, by using relatively coarse powders or particles coated with the compounds.

Other suitable agricultural compositions are wettable powders. These are finely divided particles which are dispersible in water or other liquids. The wettable powder is applied to the plant as a dry dust, or as a water or other liquid emulsion.

Carriers suitable for wettable powder formulations are Fuller's Earth, kaolin clays, silicas, and other highly absorbent, readily wettable inorganic diluents. Wettable powders generally contain about 5 to 80 weight percent of the active ingredient or ingredients, depending upon the carrier absorbency. They usually contain a small amount of a wetting dispersion, or emulsifying agent to aid dispersion.

Representative surfactants for use as wetting, dispersing, and emulsifying agents in agricultural compositions are alkyl and alkylaryl sulfonates and sulfates and their alkali salts; polyethylene oxides, sulfoxided oils, fatty acid esters of polyhydric alcohols, and other surface agents, e.g., TWEEN 20 ®, a commercial surfactant. These surfactants, if used, would vary from 0.25 to 15 weight percent of the composition.

A useful wettable powder formulation for example, comprises about 80.8 parts of bis(p-chlorophenyl)methyl methyl sulfone, 17.9 parts of attapulgite clay, and as wetting agents, 1.0 part of sodium lignosulfate and 0.3 parts of sulfonated aliphatic polyester. Another useful formulation contains 50 weight percent of the sulfone, about 40 weight percent of hydrated silica, and about 10 weight percent of emulsifiers chosen from those described above. The powder is produced by mixing the desired ingredients and milling them to a suitably fine particle size, such as 1 to 200 microns, but preferably under 74 microns.

Such wettable powder formulations may contain a mixture of the active sulfone of the general formula previously described. For example, in the formulations described above, bis(p-chlorophenyl)methyl methyl sulfone may be replaced by a mixture of sulfone compounds, but it is preferred that from 10 to 90 weight percent of the sulfone mixture be bis(p-chlorophenyl)methyl methyl sulfone, and the remainder is one or more of other preferred compounds.

All of the wettable powder formulations described may contain one or more compatible agriculturally suitable compounds such as herbicides, fertilizers, pesticides, bactericides, fungicides, or other ingredients which serve to enhance healthy growth of crops.

All of the wettable powder formulations described may be utilized, for example, by mixing the wettable powder formulation with a suitable quantity of water such as four to 20 gallons of water per pound of formulation (480 to 8,000 kilogram per cubic meter), and then applied to the crop by the use of aerial or land-based spraying equipment at practical rate, e.g., 10 to 100 gallons per acre (0.09 to 0.94 cubic meters per hectare). The spraying rate is coordinated with the amount of material to be applied in order to give the desired weight of active ingredient per unit of area.

Other suitable agricultural compositions are emulsifiable concentrates, which are liquid or paste compositions that are dispersible in water or other liquids. These types of compositions may consist of a single sulfur compound, or a mixture of the sulfone compounds and a liquid or solid emulsifying agent. They may also contain a liquid carrier, such as xylene, heavy aromatic naphthas or other nonvalatile organic solvents. The liquid or solid emulsifying agent, or surfactant may be one of those previously described.

These emulsifiable concentrates are generally dispersed in a liquid carrier, e.g., water, and applied as a spray to the foliage of the plant to be treated. The weight percent of bis(p-chlorophenyl)methyl methyl sulfone in these concentrates varies with the application procedure, but is generally from 0.5 to 95 weight percent. If a mixture of sulfones are used, then the mixture itself may vary from 0.5 to 95 weight percent of the concentrate. The amounts of the different sulfones within the mixture will vary depending upon the disease or diseases, to be treated.

While the invention has been described with reference to specific details for certain illustrative embodiments it is not intended that it shall be limited thereby except insofar as such details appear in the accompanying claims.

I claim:

1. A method of controlling the harmful effects of a fungus of the genus Piricularia upon a plant which comprises:

contacting the plant with a compound in an amount effective to control the harmful effects of the fungus upon the plant, the compound having the general formula:

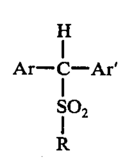

wherein:

Ar is 4-chlorophenyl

Ar′ is an aryl selected from the group consisting of 4-chlorophenyl and 2-chlorophenyl, and R is an alkyl of from one to four carbon atoms.

2. The method of claim 1, wherein R is an alkyl selected from the group consisting of methyl, ethyl, n-propyl, isopropyl and n-butyl.

3. The method as recited in claim 2, wherein the fungus is *Piricularia oryzae.*

4. The method as recited in claim 2, wherein Ar′ is 4-chlorophenyl.

5. The method as recited in claim 4, wherein the fungus is *Piricularia oryzae.*

6. The method as recited in claim 1, wherein the compound is bis(4-chlorophenyl)methyl methyl sulfone.

7. The method as recited in claim 6, wherein the fungus is *Piricularia oryzae.*

8. A method of controlling the harmful effects of a fungus of the genus Uromyces upon plants which comprises:

contacting the plant with bis(4-chlorophenyl)methyl methyl sulfone in an amount effective to control the harmful effects of the fungus upon the plant.

9. The method of claim 8, wherein the fungus is *Uromyces phaseoli typica.*

10. A method of controlling the harmful effects of a fungus of the genus Venturia upon plants which comprises:

contacting the plant with bis(4-chlorophenyl)methyl methyl sulfone in an amount effective to control the harmful effects of the fungus upon the plant.

11. The method of claim 10, wherein the fungus is *Venturia inaequalis.*

12. A method of controlling the harmful effects of a fungus of the genus Puccinia upon plants which comprises:

contacting the plant with bis(4-chlorophenyl)methyl methyl sulfone in an amount effective to control the harmful effects of the fungus upon the plant.

13. The method of claim 12, wherein the fungus is *Puccinia rubigo-vera.*

14. The method of claim 12, wherein the fungus is *Puccinia carthami.*

15. A method of controlling the harmful effects of a fungus of the genus Phytophthora upon plants which comprises:

contacting the plant with bis(4-chlorophenyl)methyl methyl sulfone in an amount effective to control the harmful effects of the fungus upon the plant.

16. The method of claim 15, wherein the fungus is *Phytophthora infestans.*

17. A method of controlling the harmful effects of a fungus of the genus Melampsora upon plants which comprises:

contacting the plant with bis(4-chlorophenyl)methyl methyl sulfone in an amount effective to control the harmful effects of the fungus upon the plant.

18. The method of claim 17, wherein the fungus is *Melampsora limi* (pera.) Desmoz.

19. A method of controlling the harmful effects of a fungus of the genus *Cochliobolus* (*Helminthosporium*) upon plants, which comprises:

contacting the plant with bis(4-chlorophenyl)methyl methyl sulfone in an amount effective to control the harmful effects of the fungus upon the plant.

20. The method of claim 17, wherein the fungus is *Cochliobolus herterostrophus* (*Helminthosporium maydis*).

* * * * *